United States Patent
Resconi et al.

(10) Patent No.: US 6,191,294 B1
(45) Date of Patent: Feb. 20, 2001

(54) PROCESS FOR THE PREPARATION OF METALLOCENE COMPOUNDS

(75) Inventors: Luigi Resconi; Davide Balboni, both of Ferrara; Giansiro Prini, Castelguglielmo, all of (IT)

(73) Assignee: Montell Technology Company BV (NE)

( * ) Notice: Under 35 U.S.C. 154(b), the term of this patent shall be extended for 0 days.

(21) Appl. No.: 09/381,075

(22) Filed: Sep. 13, 1999

(30) Foreign Application Priority Data

Jan. 14, 1998 (EP) .................................................. 98200077

(51) Int. Cl.$^7$ .............................. C07F 17/00; C07F 7/00; C07F 5/00; C07F 9/00; C07F 11/00

(52) U.S. Cl. ................... 556/11; 556/1; 556/12; 556/22; 556/43; 556/53; 556/58; 534/11; 534/15; 526/160; 526/943; 502/103; 502/117

(58) Field of Search .................. 556/1, 11, 12, 556/22, 43, 53, 58; 534/11, 15; 502/103, 117; 526/160, 943

(56) References Cited

FOREIGN PATENT DOCUMENTS

| | | |
|---|---|---|
| 129368 | 12/1984 | (EP) . |
| WO 92/00333 | * 1/1992 | (WO) . |
| WO 92/05203 | * 4/1992 | (WO) . |
| 9619488 | 6/1996 | (WO) . |
| 9843989 | 10/1998 | (WO) . |

OTHER PUBLICATIONS

L. Resconi et al., "Diastereoselective Synthesis, Molecular Structure, and Solution Dynamics of meso– and rac [Ethylenebis(4,7–dimethyl–$\eta^5$–indenyl)] Zirconium Dichloride Isomers and Chain Transfer Reactions in Propene Polymerization with the rac Isomer", *Organometallics*, 15, 5046–5059, 1996.

E. Sameul et al., "The Formation and Photolysis of bis(Fluorenyl)–Dimethylzirconium", *Journal of Organometallic Chemistry*, 113, 331–339, 1976.

F.R.W.P. Wild et al., "ansa–Metallocene Derivatives. VII–Synthesis and Crystal Structure of a Chiral ansa–Zirconocene Derivative with Ethylene–Bridged Tetrahydroindenyl Ligands", *Journal of Organometalic Chemistry*, 288, 63–67, 1985.

M. Bochmann et al., "Base–Free Cationic Zirconium Benzyl Complexes as Highly Active Polymerization Catalysts", *Organometallics*, 12, 633–640, 1993.

S. Rodewald et al., "Stereoselective Olefin Insertion Reactions of Chiral (EBI) Zr($\eta^2$–pyrid–2–yl)$^+$ and (EBTHI)Zr($\eta^2$–pyrid–2–yl)$^{30}$ Complexes", *J. Am. Chem. Soc.*, 116, 4491–4492, 1994.

I. Lee et al., "Electronic Effects in Ziegler–Natta Polymerization of Propylene and Ethylene Using Soluble Metallocene Catalysts", *Organometallics*, 11, 2115–2122, 1992.

* cited by examiner

*Primary Examiner*—Porfirio Nazario-Gonzalez

(57) ABSTRACT

A new process is disclosed, particularly simple, convenient and practical, for the direct synthesis of metallocenes of formula (I): $(CP)(ZR^1_m)_n(A)_rML_pL'_q$ wherein $(ZR^1_m)_n$ is a divalent group bridging Cp and A; Cp is a substituted or unsubstituted cyclopentadieryl group; A is —O—, —S—, —N(R$^2$)—, wherein R$^2$ is hydrogen, alkyl, cycloalkyl aryl, alkylaryl or arylalkyl, or A has the same meaning of Cp; M is a transition metal belonging to group 3, 4, 5, 6 or to the lanthanide or actinide groups; L is a monoanionic sigma ligand, such as alkyl, cycloalkyl, aryl, alkylaryl or arylalkyl, optionally containing Si or Ge; L' is halogen or —OR$^5$, R$^5$ being a hydrocarbon radical; m is 1 or 2; n is 0–4; r is 0 or 1; p is 1–3; q is 0–2. Said process comprises reacting the ligand $(Y-Cp)(ZR^1_m)_n(A-Y)_r$, wherein Y is a suitable leaving group, with at least 1 molar equivalent of ML'$_s$ in the presence of at least (1+r+p) molar equivalents of L$_j$B or LMgL', wherein B is an alkaline or alkaline-earth metal, s ranges from 3 to 6, and j is 1 or 2.

17 Claims, No Drawings

PROCESS FOR THE PREPARATION OF METALLOCENE COMPOUNDS

FIELD OF THE INVENTION

The present invention relates to a new process, particularly simple, convenient and practical, for the preparation of metallocene compounds; more specifically, it relates to a process for the direct synthesis of metallocenes wherein the transition metal atom has at least one sigma ligand selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing Si or Ge atoms. These metallocenes are useful as catalyst components, e.g. in the polymerization, oligomerization and hydrogenation of olefins, in association with alumoxanes and/or compounds able to form alkylmetallocene cations.

PRIOR ART DISCLOSURE

Homogeneous catalytic systems based on metallocenes in association with an aluminum alkyl compound or an alumoxane are well known in the state of the art and are widely used in the polymerization reaction of olefins. For instance, the European Patent Application EP 0 129 368 discloses catalysts comprising mono, di and tricyclopentadienyl coordination complexes with a transition metal and an alumoxane; more specifically, said coordination complexes are metallocene compounds of general formula:

$$(C_5R'_m)_p R''_s (C_5R'_m) MQ_{3-p}$$

wherein $(C_5R'_m)$ is an optionally substituted cyclopentadienyl group, in which 'to can be hydrogen, an alkyl, alkenyl, aryl, alkylaryl or arylalkyl radical, having from 1 to 20 carbon atoms, or two or four substituents R' on the same cyclopentadienyl group can form one or two rings, having 4 to 6 carbon atoms; R" is a divalent radical bridging the two cyclopentadienyl groups; M is a transition metal belonging to groups 4, 5 or 6 of the Periodic Table of the Elements; p is 0, 1 or 2; s is 0 or 1; m is 0 to 5; and the sigma ligands Q, same or different from each other, can be halogen atoms, alkyl, cycloalkyl, alkenyl, aryl, alkylaryl or arylalkyl radicals.

In metallocenes known in the state of the art, the sigma ligands of the central metal atom are usually halogen, preferably chlorine; also metallocene dialkyls, particularly dimethyls, have been developed and are widely used as catalyst components for olefin polymerization reactions, in association with suitable cocatalysts, such as alumoxanes and borate salts, e.g. $[Ph_3C]^+[B(C_6F_5)_4]^-$ or $[HN(n\text{-}Bu)_3]^+ [B(C_6F_5)_4]^-$. When the sigma ligands of the central metal atom are alkyl or aryl groups, the above metallocenes are usually obtained according to a process comprising the following steps:

1) preparing the metallocene dihalide, usually the metallocene dichloride, by reacting suitable ligand/s with $MX_4$, wherein X is halogen (usually $TiCl_4$ or $ZrCl_4$);

2) converting the metallocene dihalide obtained in step (1) into the corresponding dialkyl or diaryl complex, by substitution of the halogens linked to the metal atom with the desired alkyl or aryl groups, by means of an alkylating agent such as alkyllithium, dialkylmagnesium or the corresponding Grignard reagent.

Nevertheless, the above metallocenes can not be expediently synthesized by the existing methodology; in fact, prior art processes imply always the synthesis of the metallocene dihalide, that is subsequently transformed into the target product, thus leading to unsatisfactory total yields and requiring at least two process steps.

E. Samuel et al. (*J. Organomet. Chem.*, 113(4):331–339, 1976) describe the preparation of bis-fluorenyl zirconium dimethyl by treating $ZrCl_4$ with lithium fluorenyl (obtained by reacting fluorenyl and MeLi) in THF at 13 78° C., and subsequently treating the thus obtained bis-fluorenyl zirconium dichloride with MeLi. This process has the disadvantage of giving a final crude product in low total yields and it requires two reaction steps.

Even in the case of bridged metallocenes, low reaction yields are obtained. For instance, F. Wild et al. (*J. Organomet. Chem.*, 288:63–67, 1985) describe the synthesis of chiral ansa-zirconocene derivatives with ethylene-bridged ligands; in particular, it is reported the preparation of ethylenebis(1-indenyl) zirconium dichloride by reaction of the dilithium salt of bis(1-indenyl)ethane with $ZrCl_4$, in a yield of about 35%. Better results have been obtained by I. M. Lee et al. (*Organometallics*, 11:2115–2122, 1992), who prepared ethylenebis(1-indenyl) zirconium dichloride in a yield of 52%.

Furthermore, M. Bochmann and S. J. Lancaster (*Organometallics*, 12(3):633–640, 1993) report a process for the synthesis of several chiral methyl zirconocene and hafnocene complexes, and in particular the conversion of ethylenebis(1-indenyl) zirconium dichloride to the corresponding dimethyl derivative, in a yield of 21%. Better results were obtained by S. Rodewald and R. F. Jordan, who prepared ethylenebis(1-indenyl) zirconium dimethyl by reaction of the corresponding dichloride with $Me_2Mg$ in $Et_2O$ followed by work up with dioxane, with a yield of 90% (*J. Am. Chem. Soc.*, 116:4491–4492, 1994).

Therefore, according to the literature procedures, ethylenebis(1-indenyl) zirconium dimethyl can be obtained at best in two reaction steps, in an unsatisfactory total yield lower than 50% (52·90/100=46.8%).

The International Patent Application WO 96/19488 describes a method for preparing metallocene alkyls comprising, among the others, the steps of reacting a cyclopentadienyl ligand metal salt with a perhalogenated group 4–6 transition metal compound and subsequently reacting the thus obtained metallocene dihalide with at least two molar equivalents of an alkylating agent; after separation and purification procedures, metallocene alkyls are isolated.

Even in this case, two separate reaction steps are required, as well as the intermediate isolation of the dihalide metallocene, thus lowering notably the final yields and rendering the whole process more laborious and time consuming.

Therefore, the prior art processes for producing metallocene derivatives having hydrocarbon sigma ligands are inadequate for a commercially viable and practical production of said derivatives, for use as catalyst components for olefin polymerization; it is felt the need for a simpler and more convenient and practical method to produce the above metallocene derivatives in satisfactory yields.

SUMMARY OF THE INVENTION

The Applicant has now unexpectedly found a new process for the preparation of cyclopentadienyl metallocene compounds of formula (I):

$$(Cp)(ZR^1_m)_n(A)_rML_pL'_q \qquad (I)$$

wherein $(ZR^1_m)_n$ is a divalent group bridging Cp and A, Z being C, Si, Ge, N or P, and the $R^1$ groups, equal or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups;

Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;

A is —O—, —S—, —N($R^2$)—, wherein $R^2$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp;

M is a transition metal belonging to group 3, 4, 5, 6 or to the lanthanide or actinide groups of the Periodic Table of the Elements (IUPAC version);

the substituents L, same or different from each other, are monoanionic sigma ligands selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl groups, optionally containing one or more Si or Ge atoms; preferably, the substituents L are the same;

the substituents L', same or different from each other, are halogens or —$OR^5$, wherein $R^5$ has the same meaning of $R^1$;

m is 1 or 2, and more specifically it is 1 when Z is N or P, and it is 2 when Z is C, Si or Ge;

n is an integer ranging from 0 to 4;

r is 0 or 1; n is 0 when r is 0;

p is an integer ranging from 1 to 3; q is an integer ranging from 0 to 2, p+q being equal to the oxidation state of the metal M minus 2 when r=1, and minus 1 when r=0, and p+q being ≤4;

said process comprising the following steps:

(1) reacting a ligand of formula (Y—Cp)($ZR^1_m$)$_n$(A—Y)$_r$ with at least (1+r+p) molar equivalents of a compound of formula $L_j$B or LMgL', wherein Cp, A, Z, $R^1$, m, n, p, r, L and L' have the meaning reported above; the groups Y, the same or different from each other, are suitable leaving groups; B is an alkaline or alkaline-earth metal; and j is 1 or 2, j being equal to 1 when B is an alkaline metal, and j being equal to 2 when B is an alkaline-earth metal; and (2) reacting the product obtained from step (1) with at least 1 molar equivalent of a compound of formula ML'$_s$, wherein M and L' have the meaning reported above; s is an integer corresponding to the oxidation state of the metal and ranges from 3 to 6.

DETAILED DESCRIPTION OF THE INVENTION

The process of the invention allows to obtain metallocene compounds wherein the metal bears one or more sigma-bonded hydrocarbon substituents, in a simple, rapid and economic way, leading to the desired products with a one-step process starting from the suitable ligands; furthermore, said process leads to final yields much higher than the ones obtainable with the procedures known in the state of the art, therefore allowing a convenient industrial exploitation of the above metallocene compounds as catalyst components in the polymerization of olefins.

In the metallocenes of formula (I), the divalent bridge ($ZR^1_m$)$_n$ is preferably selected from the group consisting of $CR^1_2$, ($CR^1_2$)$_2$, ($CR^1_2$)$_3$, $SiR^1_2$, $GeR^1_2$, $NR^1$ and $PR^1$, $R^1$ having the meaning reported above; more preferably, said divalent bridge is Si(CH$_3$)$_2$, SiPh$_2$, CH$_2$, (CH$_2$)$_2$, (CH$_2$)$_3$ or C(CH$_3$)$_2$.

The variable m is 1 or 2; the variable n ranges from 0 to 4 and, when n>1, the atoms Z can be the same or different from each other, such as in divalent bridges —CH$_2$—O—, —CH$_2$—S— and —CH$_2$—Si(CH$_3$)$_2$—.

The ligand Cp, which is π-bonded to said metal M, is preferably selected from the group consisting of cyclopentadienyl, mono-, di-, tri- and tetra-methyl cyclopentadienyl; 4-$^t$butyl-cyclopentadienyl; 4-adamantyl-cyclopentadienyl; indenyl; mono-, di-, tri- and tetra-methyl indenyl; 4,5,6,7-tetrahydroindenyl; fluorenyl; 5,10-dihydroindeno[1,2-b]indol-10yl; N-methyl- or N-phenyl-5,10-dihydroindeno [1,2-b]indol-10-yl; 5,6-dihydroindeno[2,1-b]indol-6-yl; N-methyl-or N-phenyl-5,6-dihydroindeno[2,1-b]indol6-yl; azapentalene4-yl; thiapentalene4-yl; azapentalene-6yl; thiapentalene-6-yl; mono-, di- and tri-methyl-azapentalene4-yl.

The group A has preferably the same meaning of Cp, and more preferably is cyclopentadienyl, indenyl or tetrahydroindenyl.

The metal M is preferably Ti, Zr or Hf, and more preferably Zr.

The substituents L are preferably the same and are selected from the group consisting of $C_1$–$C_7$ alkyl groups, $C_6$–$C_{14}$ aryl groups and $C_7$–$C_{14}$ arylalkyl groups, optionally containing one or more Si or Ge atoms; more preferably, the substituents L are selected from the group consisting of methyl, ethyl, n-butyl, sec-butyl, phenyl, benzyl and —CH$_2$Si(CH$_3$)$_3$. According to a favorite embodiment of the invention, L is methyl.

The substituents L' are preferably Cl, Br or $OR^5$, wherein $R^5$ has the meaning reported above, and more preferably it is a $C_1$–$C_6$ alkyl or a $C_6$–$C_{10}$ aryl; even more preferably, L' is selected from the group consisting of Cl, —OEt, —OPr, —OBu and —OBz.

The integer n ranges from 0 to 4, and it is preferably 1 or 2.

When n=0 and r=1, A can have only the meaning of Cp; Cp and A are preferably pentamethyl cyclopentadienyl, indenyl or 4,5,6,7- tetrahydroindenyl groups. Non-limiting examples of cyclopentadienyl compounds of formula (I), wherein n=0 and r=1, are:

| | | |
|---|---|---|
| (Me$_3$Cp)$_2$MMe$_2$ | (Me$_3$Cp)$_2$MMeCl | (Me$_3$Cp)$_2$MPh$_2$ |
| (Me$_3$Cp)$_2$MBz$_2$ | (Me$_4$Cp)$_2$MMe$_2$ | (Me$_5$Cp)$_2$MMe$_2$ |
| (Me$_5$Cp)$_2$MPh$_2$ | (Me$_5$Cp)$_2$MBz$_2$ | (EtMe$_4$Cp)$_2$MMe$_2$ |
| [(C$_6$H$_5$)Me$_4$Cp]$_2$MMe$_2$ | (Et$_5$Cp)$_2$MMe$_2$ | (Ind)$_2$MMe$_2$ |
| (Ind)$_2$MMeCl(Ind)$_2$MPh$_2$ | (Ind)$_2$MPhCl | (Ind)$_2$MBz$_2$ |
| (Ind)$_2$MBzCl | (H$_4$Ind)$_2$MMe$_2$ | (H$_4$Ind)$_2$MPh$_2$ |
| (H$_4$Ind)$_2$MBz$_2$ | [(Si(CH$_3$)$_3$Cp]$_2$MMe$_2$ | |
| {[Si(CH$_3$)$_3$]$_2$Cp}$_2$MMe$_2$ and | (Me$_4$Cp)(Me$_5$Cp)MMe$_2$ | | wherein Me=methyl, Et=ethyl, Cp=cyclopentadienyl, Ind=indenyl, H$_4$Ind=4,5,6,7-tetrahydroindenyl, Ph=phenyl, Bz=benzyl, and M has the meaning reported above.

When n=1 or 2 and r=1, Cp and A, same or different from each other, are preferably cyclopentadienyl, tetramethyl-cyclopentadienyl, indenyl, 4,5,6,7-tetrahydroindenyl, 2-methyl-4,5,6,7-tetrahydroindenyl, 4,7-dimethyl- 4,5,6,7-tetrahydroindenyl, 2,4,7-trimethyl-4,5,6,7-tetrahydroindenyl or fluorenyl groups; ($ZR^1_m$)$_n$ is preferably (CH$_3$)$_2$Si, CH$_2$ or C$_2$H$_4$. Non-limiting examples of cyclopentadienyl compounds of formula (I), wherein n=1 or 2 and r=1, are:

| | |
|---|---|
| Me$_2$Si(Me$_4$Cp)$_2$MMe$_2$ | Me$_2$Si(Me$_4$Cp)$_2$MPh$_2$ |
| Me$_2$Si(Me$_4$Cp)$_2$MBz$_2$ | Me$_2$Si(Me$_4$Cp)$_2$MMeCl |
| Me$_2$C(Me$_4$Cp)(MeCp)MMe$_2$ | Me$_2$Si(Ind)$_2$MMe$_2$ |
| Me$_2$Si(Ind)$_2$MPh$_2$ | Me$_2$Si(Ind)$_2$MBz$_2$ |
| Me$_2$Si(Ind)$_2$MMeCl | C$_2$H$_4$(Ind)$_2$MMe$_2$ |
| C$_2$H$_4$(Ind)$_2$MPh$_2$ | C$_2$H$_4$(Ind)$_2$MBz$_2$ |
| C$_2$H$_4$(H$_4$Ind)$_2$MMe$_2$ | Ph(Me)Si(Ind)$_2$MMe$_2$ |
| Ph$_2$Si(Ind)$_2$MMe$_2$ | Me$_2$C(Flu)(Cp)MMe$_2$ |
| Me$_2$C(Flu)(Cp)MPh$_2$ | Me$_2$C(Flu)(Cp)MBz$_2$ |
| C$_2$H$_4$(Me$_4$Cp)$_2$MMe$_2$ | C$_2$Me$_4$(Ind)$_2$MMe$_2$ |
| Me$_2$SiCH$_2$(Ind)$_2$MMe$_2$ | Me$_2$SiCH$_2$(Ind)$_2$MPh$_2$ |
| Me$_2$SiCH$_2$(Ind)$_2$MBz$_2$ | C$_2$H$_4$(2-MeInd)$_2$MMe$_2$ |
| C$_2$H$_4$(3-MeInd)$_2$MMe$_2$ | C$_2$H$_4$(4,7-Me$_2$Ind)$_2$MMe$_2$ |
| C$_2$H$_4$(4,7-Me$_2$Ind)$_2$MPh$_2$ | C$_2$H$_4$(4,7-Me$_2$Ind)$_2$MBz$_2$ |
| C$_2$H$_4$(5,6-Me$_2$Ind)$_2$MMe$_2$ | C$_2$H$_4$(2-MeH$_4$Ind)$_2$MMe$_2$ |
| C$_2$H$_4$(2,4,7-Me$_3$H$_4$Ind)$_2$MMe$_2$ | C$_2$H$_4$(4,7-Me$_2$H$_4$Ind)$_2$MMe$_2$ |
| C$_2$H$_4$(2,4,7-Me$_3$Ind)$_2$MMe$_2$ | C$_2$H$_4$(2-Me-Benz[e]Ind)$_2$MMe$_2$ |
| C$_2$H$_4$(Benz[e]Ind)$_2$MMe$_2$ | Me$_2$Si(2-MeInd)$_2$MMe$_2$ |
| Me$_2$Si(4,7-Me$_2$Ind)$_2$MMe$_2$ | Me$_2$Si(5,6-Me$_2$Ind)$_2$MMe$_2$ |
| Me$_2$Si(2,4,7-Me$_3$Ind)$_2$MMe$_2$ | Me$_2$Si(2-MeH$_4$Ind)$_2$MMe$_2$ |
| Me$_2$Si(4,7-Me$_2$H$_4$Ind)$_2$MMe$_2$ | Me$_2$Si(2,4,7-Me$_3$H$_4$Ind)$_2$MMe$_2$ |
| Me$_2$Si(Benz[e]Ind)$_2$MMe$_2$ | Me$_2$Si(Benz[e]Ind)$_2$MPh$_2$ |
| Me$_2$Si(Benz[e]Ind)$_2$MBz$_2$  and | Me$_2$Si(2-Me-Benz[e]Ind)$_2$MMe$_2$ | wherein Me, Cp, Ind, Flu, Ph, Bz, H$_4$Ind and M has the meanings reported above.

The process according to the present invention comprises the following steps:

(1) reacting a ligand of formula (Y—Cp)(ZR$^1_m$)$_n$(A—Y)$_r$ with at least (1+r+p) molar equivalents of a compound of formula L$_j$B or LMgL', wherein Cp, A, Z, R$^1$, m, n, p, r, L and L' have the meaning reported above; the groups Y, the same or different from each other, are suitable leaving groups; B is an alkaline or alkaline-earth metal; and j is 1 or 2, j being equal to 1 when B is an alkaline metal, and j being equal to 2 when B is an alkaline-earth metal; and (2) reacting the product obtained from step (1) with at least 1 molar equivalent of a compound of formula ML'$_s$, wherein M and L' have the meaning reported above, and s is an integer corresponding to the oxidation state of the metal and ranges from 3 to 6.

The metallocene compounds of formula (I) can be finally isolated from the reaction mixture obtained in step (2) and optionally purified according to standard procedures.

Said process allows to obtain the cyclopentadienyl metallocene compounds of formula (I) in very high yields, by means of a very practical and convenient one-pot reaction.

In the ligand (Y-Cp)(ZR$^1_m$)$_n$(A-Y)$_r$, said leaving group Y is preferably selected from the group consisting of —H, —SiR$_3$ and —SnR$_3$, wherein the groups R are C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radicals.

In the reactant ML'$_s$, the metal M is preferably Ti, Zr or Hf, and the substituents L' are preferably the same and are selected from the group consisting of —Cl, —Br, —OMe, —OEt, —OPr, —OBu and —OBz; the variable s ranges from 3 to 6 and corresponds to the oxidation state of the metal M. Said reactant is preferably selected from the group consisting of TiCl$_4$, ZrCl$_4$, HfCl$_4$, ScCl$_3$, YCl$_3$, NbCl$_5$, Ti(OEt)$_4$, Ti(OPr)$_4$, Ti(OBz)$_4$, Zr(OEt)$_4$, Zr(OPr)$_4$, Zr(OBz)$_4$, Zr(OEt)$_3$Cl, Hf(OEt)$_4$, Hf(OPr)$_4$ and Hf(OBz)$_4$; it can be used even in the form of a stabilized derivative, such as an etherate complex of ML', easily available on the market.

L$_j$B and LMgL' are alkylating agents, wherein L is preferably a C$_1$–C$_7$ alkyl group, a C$_6$–C$_{14}$ aryl group, or a C$_7$–C$_{14}$ arylalkyl group, optionally substituted with Si or Ge, and more preferably L is selected from the group consisting of methyl, ethyl, n-butyl, sec-butyl, phenyl, benzyl and —CH$_2$Si(CH$_3$)$_3$; even more preferably, L is methyl.

In the compound L$_j$B, B is an alkaline or alkaline-earth metal, and preferably Li or Mg; j can be 1 or 2, as already reported.

The compound LMgL' is a Grignard reagent, wherein Mg is magnesium and L and L' have the meanings reported above; L' is preferably Cl or Br.

According to a preferred embodiment of the process of the invention, said alkylating agent is methyllithium.

According to a preferred embodiment, the process of the invention is carried out in an aprotic solvent, either polar or apolar; said aprotic solvent is preferably an aromatic or aliphatic hydrocarbon or an ether, and more preferably it is selected from the group consisting of benzene, toluene, pentane, hexane, heptane, cyclohexane, diethylether, tetrahydrofurane or mixtures thereof.

According to another embodiment of the process of the invention, in step (1), said ligand (Y—Cp)(ZR$^1_m$)$_n$(A—Y)$_r$ is previously dissolved in an aprotic solvent and to the resulting solution is added the alkylating agent L$_j$B or LMgL'; this addition is preferably carried out at a temperature ranging from –100° C. and +80° C., and more preferably from –80° C. and —20° C., over a period of 5–45 minutes, and more preferably of 10–20 minutes. The alkylating agent is preferably added in the form of a solution in one of the above mentioned aprotic solvents, and preferably by slowly dropping.

The thus obtained reaction mixture is preferably allowed to react, under stirring, for a period ranging from 1 hour to 6 hours, and more preferably from 2 hours to 3 hours, at a temperature comprised between –10° C. and +80° C., and more preferably at room temperature.

Before the reaction with ML'$_s$, in step (2), the mixture obtained from step (1) is preferably cooled to a temperature ranging from –100° C. and +80° C., and more preferably from –80° C. and –70° C.; then, ML'$_s$ is quickly added to the cooled mixture, in the form of a solution in one of the above mentioned aprotic solvents, preferably pentane.

The reaction mixture is then allowed to react for a period ranging from 6 hours to 36 hours, and more preferably from 12 hours and 18 hours, at a temperature comprised between –100° C. and +10° C., and more preferably between –50° C. and 0° C.

The thus obtained metallocene compounds of formula (I) can be isolated according to common procedures known in the state of the art. Mixtures of racemic and meso isomers can be obtained and pure isomers can be separated in high yields by using standard procedures. Therefore, the process according to the present invention allows even to obtain pure isomeric forms (racemic or meso) of said metallocene compounds, in very high yield and using a convenient one-pot reaction.

The metallocene compounds obtained with the process according to the present invention are useful in homo or co-polymerization of olefins, in particular of α-olefins of formula CH$_2$=CHR wherein R is hydrogen or a C$_1$–C$_{20}$ alkyl, such as propylene, 1-butene, 1-pentene, 4-methyl-1-pentene, 1-hexene and 1-octene, when contacted with alumoxanes and/or organometallic aluminum compounds. They can be advantageously used for the production of isotactic, syndiotactic or atactic polypropylene.

Furthermore, they are useful in the copolymerization of ethylene with cycloolefins, such as cyclopentene, cyclohexene, norbornene and 4,6-dimethyl-1-heptene, or in ethylene copolymerization with polyenes, such as 1,4-hexadiene, isoprene, 1,3-butadiene, 1,5-hexadiene and 1,6-heptadiene.

Finally, they can be advantageously used in olefin oligomerization and hydrogenation reactions.

The above metallocenes form suitable polymerization catalytic systems in association with alumoxanes of formula:

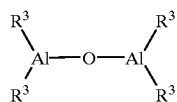

wherein the substituents R$^3$ can be a linear or branched, saturated or unsaturated, C$_{1-C20}$ alkyl, alkenyl or alkylaryl radical;

or in association with an organometallic aluminum compound of formula AlR$^4_{3-z}$H$_z$, wherein R$^4$ can be C$_1$–C$_{10}$-alkyl, alkenyl or alkylaryl radicals, optionally containing one or more Si or Ge atoms, and water.

Particularly suitable alumoxanes, acting as cocatalysts with the above metallocenes, are methylalumoxane (MAO), tris(2-methyl-propyl)alumoxane (TIBAO) and 2,4,4-trimethyl-pentylalumoxane (TIOAO).

Non-limiting examples of organometallic aluminum are trimethylaluminum (TMA), tris(2,4,4-trimethyl-pentyl) aluminum (TIOA), tris(2-methyl-propyl)aluminum (TIBA), tris(2,3,3-trimethyl-butyl)aluminum, tris(2,3-dimethyl-hexyl)aluminum, tris(2,3dimethyl-butyl)aluminum, tris(2,3-dimethyl-pentyl)aluminum, tris(2,3-dimethyl-heptyl) aluminum, tris(2-methyl-3-ethyl-pentyl)aluminum and tris (2-ethyl-3,3-dimethyl-butyl).

Other suitable cocatalysts are compounds capable of forming a metallocene cation, having formula Y$^+$Z$^-$, wherein Y$^+$ is a Brønsted acid (such as Ph$_3$C$^+$ or HN$^+$(n-Bu)$_3$) and Z$^-$ is a non-coordinating anion (such as [B(C$_6$F$_5$)$_4$]$^-$=tetrakis-pentafluorophenyl borate), able to stabilize the active catalyst species and sufficiently labile to be displaced by an olefinic substrate.

The above catalysts can be used on inert supports, such as silica, alumina, styrene/divinylbenzene copolymers, polyethylene or polypropylene, particularly suitable in gas phase polymerizations.

The polymerization processes can be carried out in liquid phase, optionally in the presence of an inert hydrocarbon solvent either aromatic (e.g. toluene) or aliphatic (e.g. propane, hexane, heptane, isobutane, cyclohexane and 2,2, 4trimethylpentane). The polymerization temperature generally ranges from about 0° C. to about 250° C., and preferably from 20 to 150° C.

The following examples are given for illustrative and not limitative purposes.

GENERAL PROCEDURES AND CHARACTERIZATIONS

All the operations were performed under nitrogen by using conventional Schienk-line techniques. Solvents were distilled from blue Na-benzophenone ketyl (Et$_2$O) and from AliBu$_3$ (pentane and toluene), and subsequently stored under nitrogen. MeLi (Aldrich) was used as received.

All compounds were analyzed by $^1$H-NMR (CD$_2$Cl$_2$ referenced against the middle peak of the triplet of residual CHDCl$_2$ at 5.35 ppm; C$_6$D$_6$, referenced against residual C$_6$D$_5$H at 7.15 ppm) on a DPX200 Bruker spectrometer. All NMR solvents were dried over P$_2$O$_5$ and distilled before use. Preparation of the samples was carried out under nitrogen, using standard inert atmosphere techniques.

EXAMPLE 1

Synthesis of rac-CH$_2$(3-tert-butyl-1-indenyl)$_2$ZrMe$_2$.

The compound rac-CH$_2$(3-$^t$Bu-1-Ind)$_2$ZrMe$_2$ was prepared with the process of the invention, according to the following reaction scheme:

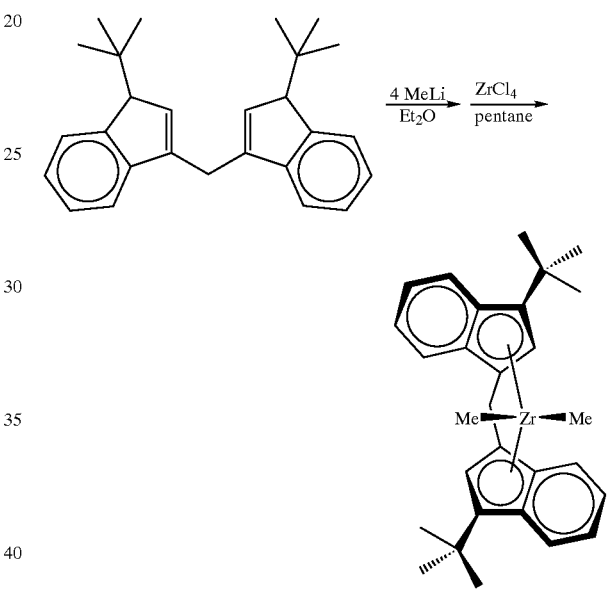

The ligand bis-(3-tetra-butyl-1-indenyl)methane was prepared by the base-catalyzed condensation of indene with formaldehyde, as described in Example 3 (a) and (b) of the European Patent Application No.97200933.6.

6.0 g of pure bis(3-tert-butyl-1-indenyl)methane (MW 356, 15.8 mmol) were dissolved in 120 mL Et$_2$O in a 250 mL Schlenk tube, and the solution cooled to −20° C. 45 mL of 1.6 M MeLi in Et$_2$O (72 mmol) were added dropwise, over 15 minutes, under continuous stirring. The solution was allowed to warm to room temperature and stirred for 5 hours. After about 1.5 hours, the lithium salt started to precipitate with final formation of an orange suspension.

4.0 g of ZrCl$_4$ (MW 233.03, 17.0 mmol) were suspended in 120 mL pentane. The two mixtures were both cooled to −80° C. and the Li salt solution in Et$_2$O was quickly added to the ZrCl$_4$ slurry in pentane; the resulting mixture was stirred for 30 minutes at −80° C. The cooling bath was removed. The reaction mixture was stirred overnight (about 16 hours) at room temperature. The black mixture thus obtained was brought to dryness under reduced pressure. The resulting black powder was suspended in 100 mL of pentane and transferred into a filtration apparatus equipped with side arm (to allow solvent refluxing), connecting the system above and below the frit, a receiving flask on the bottom and bubble condenser on the top. The filtered 100 mL pentane solution (A) were separated and the remaining solid was extracted with refluxing pentane for about 6 hours. The obtained filtrate was added to the above pentane solution (A) and the resulting solution was evaporated to dryness under reduced pressure to give 5.6 g of yellow-brown powder which contained the target rac-CH$_2$(3-$^t$Bu-Ind)$_2$ZrMe$_2$ as the major product, contaminated by about 5% of its meso isomer, with some polymeric byproducts.

Said brown-yellow solid was washed with Et$_2$O until it became yellow. The Et$_2$O washing was discarded and the residue was dried to yield a yellow solid (yield=30%) consisting of pure rac-CH$_2$(3-$^t$Bu-1-Ind)$_2$ZrMe$_2$ ($^1$H NMR analysis).

$^1$H NMR (d, ppm, C$_6$D$_6$): CH$_3$, s, −0.82, 6H; $^t$Bu, s, 1.39, 18H; —CH$_2$—, s, 3.84, 2H; Cp—H, s, 5.49, 2H; Ar, t,d,t, 6.7–7.2, 6H; d, 7.7–7.8, 2H.

COMPARATIVE EXAMPLE 1

Synthesis of rac-CH$_2$(3-tert-butyl-1-indenyl)$_2$ZrCl$_2$.

The synthesis of methylene-bis(3-tert-butyl-1-indenyl)-zirconium dichloride from the ligand bis-(3-tert-butyl-1-indenyl)methane was carried out as described in Example 3(c) of the European Patent Application No.97200933.6, according to the following reaction scheme:

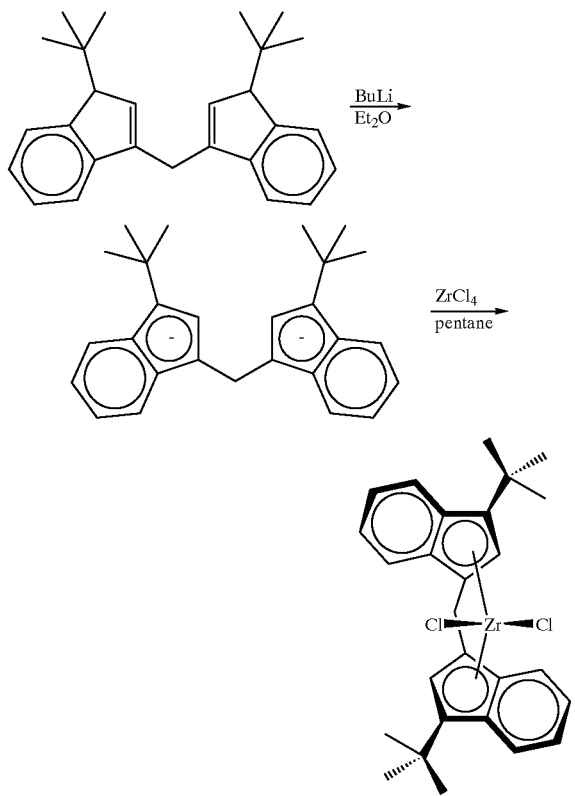

The product rac-CH$_2$(3-tert-butyl-1-indenyl)$_2$ZrCl$_2$ was obtained with a yield of 52%.

Synthesis of rac-CH$_2$(3-tert-butyl-1-indenyl)$_2$ZrMe$_2$.

The Applicant carried out the conversion of rac-CH$_2$(3-tert-butyl-1-indenyl)$_2$ZrCl$_2$ to rac-CH$_2$(3-tert-butyl-1-indenyl)$_2$ZrMe$_2$, according to the procedures known in the state of the art.

3.06 ml of a solution of methyllithium 1.6 M (4.9 mmoles) in Et$_2$O were added, at the temperature of −78° C., over a period of about 10 minutes, to a solution containing 1.2 g (9.23 mmoles) of rac-CH$_2$(3-tert-butyl-1-indenyl)$_2$ZrCl$_2$ in 50 mL of Et$_2$O.

The reaction mixture was stirred, at room temperature, for 24 hours, and a dark brown solution was finally obtained. The reaction mixture was then brought to dryness under reduced pressure, thus isolating a brown solid, which was extracted with pentane; the filtrate was evaporated to dryness under reduced pressure, thus giving 0.56 g (51% yield) of a pale yellow solid, which was identified at the $^1$H-NMR analysis as chemically pure rac-CH$_2$(3-tert-butyl-1-indenyl)$_2$ZrMe$_2$.

Therefore, rac-CH$_2$(3-tert-butyl-1-indenyl)$_2$ZrMe$_2$ was obtained from the ligand bis-(3-tert-butyl-indenyl)methane with a total yield of 26.5% (52.51:100=26.52). Said yield is much lower than the one obtained with the process according to the present invention, which has also the huge advantage of being a one-step synthesis, while the prior art procedures require at least two reaction steps.

EXAMPLE 2

Synthesis of Ethylenebis(4,7-dimethyl-1-indenyl) Zirconium Dimethyl

Using darkened glassware, 8.4 ml of a solution of MeLi 1.6 M in Et$_2$O (13.44 mmoles) were added, at the temperature of −70° C., over a period of about 10 minutes, to a solution containing 1 g of 1,2-bis(4,7-dimethyl-indenyl) ethane (3.2 mmoles) in 30 mL of Et$_2$O. The mixture was allowed to warm slowly to room temperature and maintained under stirring for 3 hours. An increasing turbidity was observed, with the final formation of a white suspension.

To said suspension, cooled to −80° C., was quickly added a mixture of 0.746 g of ZrCl$_4$ (3.2 mmol) in 30 mL pentane, previously cooled to −80° C. too. The temperature was allowed to warm slowly to room temperature overnight (about 16 hours) and a dark brown solution was finally obtained. The reaction mixture was then brought to dryness under reduced pressure. The thus obtained brown solid was extracted with 40 mL of toluene and then the filtrate was evaporated to dryness under reduced pressure, thus giving 1.12 g (80.7 % yield) of a pale yellow solid.

The $^1$H-NMR analysis showed the presence of chemically pure ethylenebis-(4,7-dimethyl-1-indenyl) zirconium dimethyl (rac:meso=2,84:1).

$^1$H NMR rac (d, ppm, C$_6$D$_6$): CH$_3$,s,−0.98, 6H; CH$_3$-ring, s, 2.23 6H; CH$_3$-ring, s, 2.31 6H; —CH$_2$—, m, 2.80–2.85, 2H; —CH$_2$—, m, 3.27–3.32, 2H; Cp-H, d, 5.75, 2H, d, 6.70, 2H; Ar, d, 6.59, 2H, d, 6.785, 2H.

$^1$H NMR meso (d, ppm, C$_6$D$_6$): CH$_3$,s,−2.10, 3H; CH$_3$, s,−0.042, 3H; CH$_3$-ring, d, 2.315 12H; —CH$_2$—, m, 2.67–2.78, 2H; —CH$_2$—, m, 3.23–3.34, 2H; Cp-H, d, 5.83, 2H, d, 6.51, 2H; Ar, s, 6.67, 4H.

COMPARATIVE EXAMPLE 2

Synthesis of Ethylenebis(4,7-dimethyl-1-indenyl) Zirconium Dichloride

Ethylenebis(4,7-dimethyl-1-indenyl) zirconium dichloride was prepared by reacting 1,2-bis(4,7-dimethyl-indenyl) ethane with ZrCl$_4$, as reported by L. Resconi et al.

(*Organometallics*, Vol.15, No.23, page 5057, 1996), thus obtaining a mixture of racemic and meso isomers in a total yield of 43.8%.

Synthesis of Ethylenebis(4,7-dimethyl-1-indenyl) Zirconium Dimethyl

Using darkened glassware, 12.11 ml of a solution of methyllithium 1.6 M (19.38 mmoles) in $Et_2O$ were added, at the temperature of −40° C., over a period of about 10 minutes, to a solution containing 4.38 g (9.23 mmoles) of ethylenebis(4,7-dimethyl-1-indenyl) zirconium dichloride, prepared as reported above, in 80 mL of $Et_2O$.

The reaction mixture was allowed to warm slowly to room temperature overnight (about 16 hours) and a dark brown solution was finally obtained. The reaction mixture was then brought to dryness under reduced pressure. The brown solid was extracted with 40 mL of toluene and then the filtrate was evaporated to dryness under reduced pressure, thus giving 1.52 g (37.9% yield) of a pale yellow solid, that at the $^1$H-NMR analysis resulted to be chemically pure ethylenebis(4,7-dimethyl 1-indenyl) zirconium dimethyl.

Therefore, according to the instant comparative example, ethylenebis(4,7-dimethyl 1-indenyl) zirconium dimethyl was obtained from the ligand 1,2-bis(4,7-dimethyl-indenyl) ethane in a total yield lower than 20% (43.8·37.9:100=16.6).

Even in this case, the processes known in the state of the art, besides having the disadvantage of requiring at least two reaction steps (while the process of the invention is a one-step synthesis), give product yields much lower than the process of the present invention.

EXAMPLE 3

Synthesis of Ethylenebis(1-indenyl) Zirconium Dimethyl

Using darkened glassware, 8.4 ml of a solution of MeLi 1.6 M in $Et_2O$ (13.44 mmoles) were added, at the temperature of −70° C., over a period of about 10 minutes, to a solution containing 0.82 g of bis(indenyl)ethane (3.2 mmoles; 90% of G.C. purity) in 30 ml of $Et_2O$. The mixture was allowed to warm slowly to room temperature and stirred for 3 hours. An increasing turbidity was observed, with the final formation of a white suspension.

To said white suspension, cooled to −80° C., was quickly added a mixture of 0.746 g of $ZrCl_4$ (3.2 mmoles) in 30 ml pentane, previously cooled to −80° C. The temperature was allowed to warm slowly to room temperature overnight (about 16 hours) and a dark brown solution was finally obtained. The reaction mixture was then brought to dryness under reduced pressure. The brown solid was extracted with 40 ml of toluene and then the filtrate was evaporated to dryness under reduced pressure, thus giving 0.67 g (61.6% yield) of a pale yellow solid. The $^1$H-NMR analysis showed the presence of chemically pure ethylenebis(1-indenyl) zirconium dimethyl (rac:meso=0.5:1).

$^1$H NMR rac (d,ppm, $C_6D_6$): $CH_3$,s,−0.95, 6H; —$CH_2$—, m, 2.6–2.8, 4H; Cp-H, d, 5.75, 2H, d, 6.70, 2H; Ar, m, 6.9–7.4, 8H.

$^1$H NMR meso (d,ppm, $C_6D_6$): $CH_3$,s,−2.19, 3H; $CH_3$, s,−0.13, 3H; —$CH_2$—, m, 3.03–3.1, 4H; Cp—H, d, 5.83, 2H, d, 6.46, 2H; Ar, m, 6.8–7.04, 8H.

The reaction yield of ethylenebis(1-indenyl) zirconium dimethyl, obtained with the one-step process according to the present invention, is much higher than the one obtainable with the two reaction steps according to the literature procedures (lower than 50%), as already reported in the prior art description.

EXAMPLE 4

Synthesis of Isopropylidenebis(1-indenyl) Zirconium Methylchloride

Using darkened glassware, 10.23 ml of a solution of MeLi 1.6 M in $Et_2O$ (16.38 mmoles) were added, at the temperature of −70° C., over a period of about 10 minutes, to a solution containing 1.062 g of 2,2-bis(indenyl)propane (3.9 mmoles) in 30 ml of $Et_2O$. The mixture was allowed to warm slowly to room temperature and stirred for 3 hours. An increasing turbidity was observed, with the final formation of an orange suspension.

To said orange suspension, cooled to −80° C., was quickly added a mixture of 0.909 g of $ZrCl_4$ (3.9 mmoles) in 30 ml pentane, previously cooled to −80° C. The temperature was allowed to warm slowly to room temperature overnight (about 16 hours) and a dark brown solution was finally obtained. The reaction mixture was then brought to dryness under reduced pressure. The brown solid was extracted with 40 ml of toluene and then the filtrate was evaporated to dryness under reduced pressure, thus giving 0.88 g (80.7% yield) of a yellow solid. The $^1$H-NMR analysis showed the presence of chemically pure isopropylidenebis(1-indenyl) zirconium methylchloride (rac:meso=2.49:1).

EXAMPLE 5

Synthesis of Bis-indenyl Zirconium Dimethyl

Using darkened glassware, 7.7 ml of a solution of MeLi 1.6 M in $Et_2O$ (12.32 mmoles) were added, at the temperature of −70° C., over a period of about 5 minutes, to a solution containing 0.68 g of indene (5.85 mmoles) in 25 ml of $Et_2O$. The mixture was allowed to warm slowly to room temperature and stirred for 5 hours. An increasing turbidity was observed, with the final formation of an orange suspension.

To said orange suspension, cooled to −80° C., was quickly added a mixture of 0.682 g of $ZrCl_4$ (2.92 mmoles) in 25 ml pentane, previously cooled to −80° C. The temperature was allowed to warm slowly to room temperature overnight (about 16 hours) and a dark brown solution was finally obtained. The reaction mixture was then brought to dryness under reduced pressure. The brown solid was extracted with 40 ml of toluene and then the filtrate was evaporated to dryness under reduced pressure, thus giving 0.597 g (58.2% yield) of an orange solid. The $^1$H-NMR analysis showed the presence of chemically pure bis-indenyl zirconium dimethyl.

$^1$H NMR (d,ppm, $C_6D_6$): $CH_3$,s,−0.77, 6H; Cp—H, t, 5.62, 2H; Cp—H, d, 5.80, 4H; Ar, m, 6.90, 4H; Ar, m, 7.21, 4H.

EXAMPLE 6

Synthesis of (tert-butylamido)(dimethyl) (tetramethyl-$\eta^5$-cyclopentadienyl)Silane Zirconium Dimethyl 12.16 ml of a solution of MeLi 1.6 M in $Et_2O$ (19.46 mmoles) were added, at room temperature, over a period of about 5 minutes, to a solution containing 1.16 g (4.63 mmoles) of (tert-butylamido)(dimethyl)(tetramethyl-cyclopentadi-2,4-enyl)silane in 25 ml of $Et_2O$. The mixture was stirred for 2 hours. An increasing turbidity was observed, with the final formation of a white suspension.

To said white suspension was quickly added, at room temperature, a mixture of 1.08 g of $ZrCl_4$ (4.63 mmoles) in 25 ml pentane. The mixture was stirred overnight and a brown solution was finally obtained. The reaction mixture was then brought to dryness under reduced pressure. The brown solid was extracted with 60 ml of toluene and then the filtrate was evaporated to dryness under reduced pressure to give 1.52 g (88.8% yield) of a brown solid. $^1$H-NMR showed the presence of chemically pure (tert-butylamido)(dimethyl)(tetramethyl-$\eta^5$-cyclopentadienyl)silane zirconium dimethyl.

$^1$H NMR ($\delta$, ppm, $C_6D_6$): (Zr)$CH_3$, s, −0.11, 6H; (Si)$CH_3$, s, 0.47, 6H; t-But, s, 1.41, 9H; (Cp)$CH_3$, s, 1.92, 6H; (Cp)$CH_3$, s, 1.98, 6H.

What is claimed is:

1. A process for the preparation of cyclopentadienyl metallocene compounds of formula (I):

(I)

wherein $(ZR^1_m)_n$ is a divalent group bridging Cp and A, Z being C, Si, Ge, N or P, and the $R^1$ groups, same or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups;

Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;

A is —O—, —S—, —N($R^2$)—, wherein $R^2$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp;

M is a transition metal belonging to group 3, 4, 5, 6 or to the lanthanide or actinide groups of the Periodic Table of the Elements (IUPAC version);

the substituents L, same or different from each other, are monoanionic sigma ligands selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl groups, optionally containing one or more Si or Ge atoms;

the substituents L', same or different from each other, are halogens or —$OR^5$, wherein $R^5$ has the same meaning of $R^1$;

m is 1 or 2; n ranges from 0 to 4; r is 0 or 1; n is 0 when r is 0; p ranges from 1 to 3; q ranges from 0 to 2, p+q being equal to the oxidation state of the metal M minus 2 when r=1, and minus 1 when r=0, and p+q being ≦4;

said process being characterized by comprising the following steps:

(1) reacting a ligand of formula (Y—Cp)($ZR^1_m)_n$(A—Y)$_r$ with at least (1+r+p) molar equivalents of a compound of formula $L_jB$ or LMgL', wherein Cp, A, Z, $R^1$, m, n, p, r, L and L' have the meaning reported above; the groups Y, the same or different from each other, are suitable leaving groups; B is an alkaline or alkaline-earth metal; and j is 1 or 2, j being equal to 1 when B is an alkaline metal, and j being equal to 2 when B is an alkaline-earth metal; and (2) reacting the product obtained from step (1) with at least 1 molar equivalent of a compound of formula $ML'_s$, wherein M and L' have the meaning reported above; s is an integer corresponding to the oxidation state of the metal and ranges from 3 to 6.

2. The process according to claim 1, wherein $(ZR^1_m)_n$ is selected from the group consisting of $CR^1_2$, $(CR^1_2)_2$, $(CR^1_2)_3$, $SiR^1_2$, $GeR^1_2$, $NR^1$ and $PR^1$, $R^1$ having the meaning reported in claim 1.

3. The process according to claim 1, wherein Cp is selected from the group consisting of cyclopentadienyl; mono-, di-, tri- and tetra-methyl cyclopentadienyl; 4-$^t$butyl-cyclopentadienyl; 4-adamantyl-cyclopentadienyl; indenyl; mono-, di-, tri- and tetra-methyl indenyl; 4,5,6,7-tetrahydroindenyl; fluorenyl; 5,10-dihydroindeno[1,2-b]indol-10-yl; N-methyl- or N-phenyl-5,10-dihydroindeno[1,2-b]indol-10-yl; 5,6-dihydroindeno[2,1-b]indol-6-yl; N-methyl-or N-phenyl-5,6-dihydroindeno[2,1-b]indol-6-yl; azapentalene4-yl; thiapentalene-4-yl; azapentalene-6-yl; thiapentalene-6-yl; mono-, di- and tri-methyl-azapentalene-4-yl; and A has the same meaning of Cp.

4. The process according to claim 1, wherein M is Ti, Zr or Hf.

5. The process according to claim 1, wherein the substituents L are the same and are selected from the group consisting of methyl, ethyl, n-butyl, sec-butyl, phenyl, benzyl and —$CH_2Si(CH_3)_3$.

6. The process according to claim 1 wherein L' is selected from the group consisting of Cl, Br, —OMe, —OEt, —OPr, —OBu and —OBz.

7. The process according to claim 1, wherein $ML'_s$ is selected from the group consisting of $TiCl_4$, $ZrCl_4$, $HfCl_4$, $ScCl_3$, $YCl_3$, $NbCl_5$, $Ti(OEt)_4$, $Ti(OPr)_4$, $Ti(OBz)_4$, $Zr(OEt)_4$, $Zr(OPr)_4$, $Zr(OBz)_4$, $Zr(OEt)_3Cl$, $Hf(OEt)_4$, $Hf(OPr)_4$, $Hf(OBz)_4$ and etherate complexes thereof.

8. The process according to claim 1 wherein, in the compound $L_jB$ or LMgL', L is selected from the group consisting of methyl, ethyl, n-butyl, sec-butyl, phenyl, benzyl and —$CH_2Si(CH_3)_3$; B is Li or Mg; and L' is Cl or Br.

9. The process according to claim 8, characterized by the fact that L is methyl.

10. The process according to claim 1, characterized by being carried out in at least an aprotic solvent.

11. The process according to claim 10, wherein said aprotic solvent is an aromatic or aliphatic hydrocarbon selected from the group consisting of benzene, toluene, pentane, hexane, heptane and cyclohexane, or is an ether selected from the group consisting of diethylether and tetrahydrofurane.

12. The process according to claims 1 and 10, characterized in that, in step (1), said ligand (Y—Cp)($ZR^1_m)_n$(A—Y)$_r$ is first dissolved in said aprotic solvent and to the resulting solution is added $L_jB$ or LMgL', at a temperature ranging from −100° C. and +80° C., over a period of 5–45 minutes, and finally $ML'_s$ is added.

13. The process according to claim 12, characterized in that said $L_jB$ or $LM_gL'$ is added in the form of a solution in said aprotic solvent.

14. The process according to claim 12, characterized in that, in step (1), after the addition of $L_jB$ or LMgL', the obtained reaction mixture is allowed to react, under stirring, for a period ranging from 1 hour to 6 hours, at a temperature comprised between −10° C. and +80° C.

15. The process according to claim 12, characterized in that, in step (2), before the reaction with $ML'_s$, the mixture obtained from step (1) is cooled to a temperature ranging from −100° C. and +80° C.

16. The process according to claim 15, characterized in that $ML'_s$ is in the form of a solution in an aprotic solvent.

17. The process according to claim 15, characterized in that, in step (2), the reaction mixture is allowed to react for a period ranging from 6 hours to 36 hours, at a temperature comprised between −100° C. and +10° C.

* * * * *

UNITED STATES PATENT AND TRADEMARK OFFICE
CERTIFICATE OF CORRECTION

PATENT NO. : 6,191,294 B1
DATED : February 20, 2001
INVENTOR(S) : Luigi Resconi et al.

It is certified that error appears in the above-identified patent and that said Letters Patent is hereby corrected as shown below:

Column 14,
Line 43, change "$(Y\text{-}Cp)(ZR^1_m)_n(A\text{-}Y),$" to -- $(Y\text{-}Cp)(ZR^1_m)_n(A\text{-}Y)_r$ --.

Signed and Sealed this

Eighteenth Day of October, 2005

JON W. DUDAS
*Director of the United States Patent and Trademark Office*